(12) United States Patent
Lenser et al.

(10) Patent No.: US 12,358,269 B2
(45) Date of Patent: Jul. 15, 2025

(54) METHODS AND APPARATUSES FOR ASSEMBLING ELASTIC LAMINATES WITH A ROTATING ROLL AND REMOVABLE LAYER

(71) Applicant: The Procter & Gamble Company, Cincinnati, OH (US)

(72) Inventors: Todd Douglas Lenser, Liberty Township, OH (US); Justin B. Owens, Ft. Thomas, KY (US); Jeffry Rosiak, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 32 days.

(21) Appl. No.: 18/541,301

(22) Filed: Dec. 15, 2023

(65) Prior Publication Data

US 2024/0116284 A1  Apr. 11, 2024

Related U.S. Application Data

(63) Continuation of application No. 17/860,120, filed on Jul. 8, 2022, now Pat. No. 11,878,497.
(Continued)

(51) Int. Cl.
*B32B 37/00* (2006.01)
*B32B 37/06* (2006.01)
(Continued)

(52) U.S. Cl.
CPC ........ *B32B 37/0053* (2013.01); *B32B 37/065* (2013.01); *B32B 37/20* (2013.01);
(Continued)

(58) Field of Classification Search
None
See application file for complete search history.

(56) References Cited

U.S. PATENT DOCUMENTS 5,277,437 A * 1/1994 Moats ............... A63C 17/0086
280/11.233
6,170,393 B1 * 1/2001 Hook ............... A61F 13/15707
101/6

(Continued)

FOREIGN PATENT DOCUMENTS

| CA | 2470416 A1 | 7/2003 |
| EP | 3501802 A1 | 6/2019 |
| WO | 9959512 A1 | 11/1999 |

OTHER PUBLICATIONS

Extended EP Search Report and Written Opinion for 22183755.2 dated Dec. 7, 2022, 08 pages.
(Continued)

*Primary Examiner* — Michael N Orlando
*Assistant Examiner* — Abhishek A Patwardhan
(74) *Attorney, Agent, or Firm* — Daniel S. Albrecht

(57) ABSTRACT

A method for ultrasonically bonding elastic laminates is provided. The method includes attaching a removable shell layer to at least a portion of an exterior surface of a rotating roll, advancing at least a laminate material assembly along a machine direction to dispose the laminate material assembly on the removable shell layer, applying a vacuum pressure to the laminate material assembly, ultrasonically bonding the laminate material assembly, and advancing the elastic laminate including the laminate pattern along the machine direction.

20 Claims, 6 Drawing Sheets

Related U.S. Application Data

(60) Provisional application No. 63/220,060, filed on Jul. 9, 2021.

(51) Int. Cl.
  *B32B 37/20*   (2006.01)
  *B32B 38/18*   (2006.01)

(52) U.S. Cl.
  CPC ...... *B32B 38/1858* (2013.01); *B32B 2307/51* (2013.01); *B32B 2310/028* (2013.01); *B32B 2555/02* (2013.01)

(56) References Cited

U.S. PATENT DOCUMENTS

| | | | | |
|---|---|---|---|---|
| 2005/0039859 | A1* | 2/2005 | Sugaya | B32B 37/0053 156/583.1 |
| 2017/0266059 | A1* | 9/2017 | Long | A61F 13/15747 |
| 2020/0095084 | A1* | 3/2020 | Fritz | B32B 37/0053 |

OTHER PUBLICATIONS

All Office Actions; U.S. Appl. No. 17/860,120, filed Jul. 8, 2022.
U.S. Appl. No. 17/860,120, filed Jul. 8, 2022, to Todd Douglas Lenser et al.

* cited by examiner

METHODS AND APPARATUSES FOR ASSEMBLING ELASTIC LAMINATES WITH A ROTATING ROLL AND REMOVABLE LAYER

CROSS-REFERENCE TO RELATED APPLICATIONS

This application is a continuation of, and claims priority under 35 U.S.C. § 120 to, U.S. patent application Ser. No. 17/860,120, filed on Jul. 8, 2022, which claims the benefit, under 35 USC 119(e), to U.S. Provisional Patent Application No. 63/220,060, filed on Jul. 9, 2021; each of which are herein incorporated by reference in their entirety.

TECHNICAL FIELD

The present disclosure relates to apparatuses and methods for assembling elastic laminates and more particularly, to apparatuses and methods for a rotating roll with a removable layer for assembling elastic laminates.

BACKGROUND

Along an assembly line, various types of articles, such as for example, diapers and other absorbent articles, may be assembled by adding components to and/or otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. In some cases, individual components created from an advancing web or webs are combined with other individual components created from other advancing web or webs. Webs of material and component parts used to manufacture diapers may include: backsheets, topsheets, leg cuffs, waist bands, absorbent core components, front and/or back ears, and fastening components. Once the desired component parts are assembled, the advancing web(s) and component parts may be subjected to a final knife cut to separate the web(s) into discrete diapers or other absorbent articles.

Some diaper components, such as leg elastics, barrier leg cuff elastics, stretch side panels, and waist elastics, are constructed from elastic laminates. Such elastic laminates may be assembled in various ways depending on the particular diaper design. For example, some elastic laminates may be constructed from one or more nonwoven substrates bonded to an elastic film. In some configurations, the elastic film may be stretched and then bonded with the nonwoven substrates to form an elastic laminate.

Desirable need exists to provide improved, more efficient, and more adaptable assemblies and methods for manufacturing absorbent articles.

SUMMARY

In one embodiment, a system for ultrasonic bonding of elastic laminates includes a rotating roll having an axis of rotation and an exterior surface. The exterior surface is formed radially about the axis of rotation of the rotating roll and includes one or more roll anchoring mechanisms. The system further includes a removable shell layer that includes one or more patterned segments configured to removably attach to at least a portion of the exterior surface of the rotating roll. The one or more patterned segments include a plurality of shell channels formed through the removable shell layer to form a pattern. The one or more patterned segments further includes an anchoring mechanism configured to anchor and fasten each patterned segment to at least one of the one or more roll anchoring mechanisms of the rotating roll.

In yet another embodiment, a rotating roll for ultrasonic bonding of elastic laminates is described. The rotating roll includes an exterior surface formed radially about an axis of rotation of the rotating roll. The rotating roll further includes a vacuum source disposed within the rotating roll and configured to automate a vacuum action about the axis of rotation of the rotating roll. Further, the rotating roll includes plurality of vacuum apertures disposed on the exterior surface in communication with the vacuum source to enable the vacuum action. The plurality of vacuum apertures are configured to align with a corresponding plurality of apertures in a removable shell layer to form a vacuum path such that the vacuum action occurs through the vacuum path. The rotating roll includes a plurality of magnets, mechanical anchoring mechanisms, or combinations thereof disposed at least one of within or on the exterior surface. The plurality of magnets, mechanical anchoring mechanisms, or combinations thereof are configured to attach to the removable shell layer to fasten the removable shell layer to the rotating roll.

In another embodiment, a method for ultrasonically bonding elastic laminates includes attaching a removable shell layer including a plurality of shell channels to form a shell pattern to at least a portion of an exterior surface of a rotating roll. The rotating roll includes an axis of rotation. The exterior surface is formed radially about the axis of rotation. The method further includes advancing at least a laminate material assembly along a machine direction to dispose the laminate material assembly on the removable shell layer. The laminate material assembly includes a pair of substrate materials with at least an elastic material positioned therebetween. The method further includes applying a vacuum pressure to the laminate material assembly through a plurality of roll channels of the rotating roll aligned with the plurality of shell channels of the removable shell layer to draw the laminate material assembly into the plurality of shell channels forming the shell pattern. The method further includes ultrasonically bonding the laminate material assembly to bond the pair of substrate materials and the elastic material positioned therebetween to form an elastic laminate including a laminate pattern corresponding to the shell pattern, and advancing the elastic laminate including the laminate pattern along the machine direction.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Figure 1:
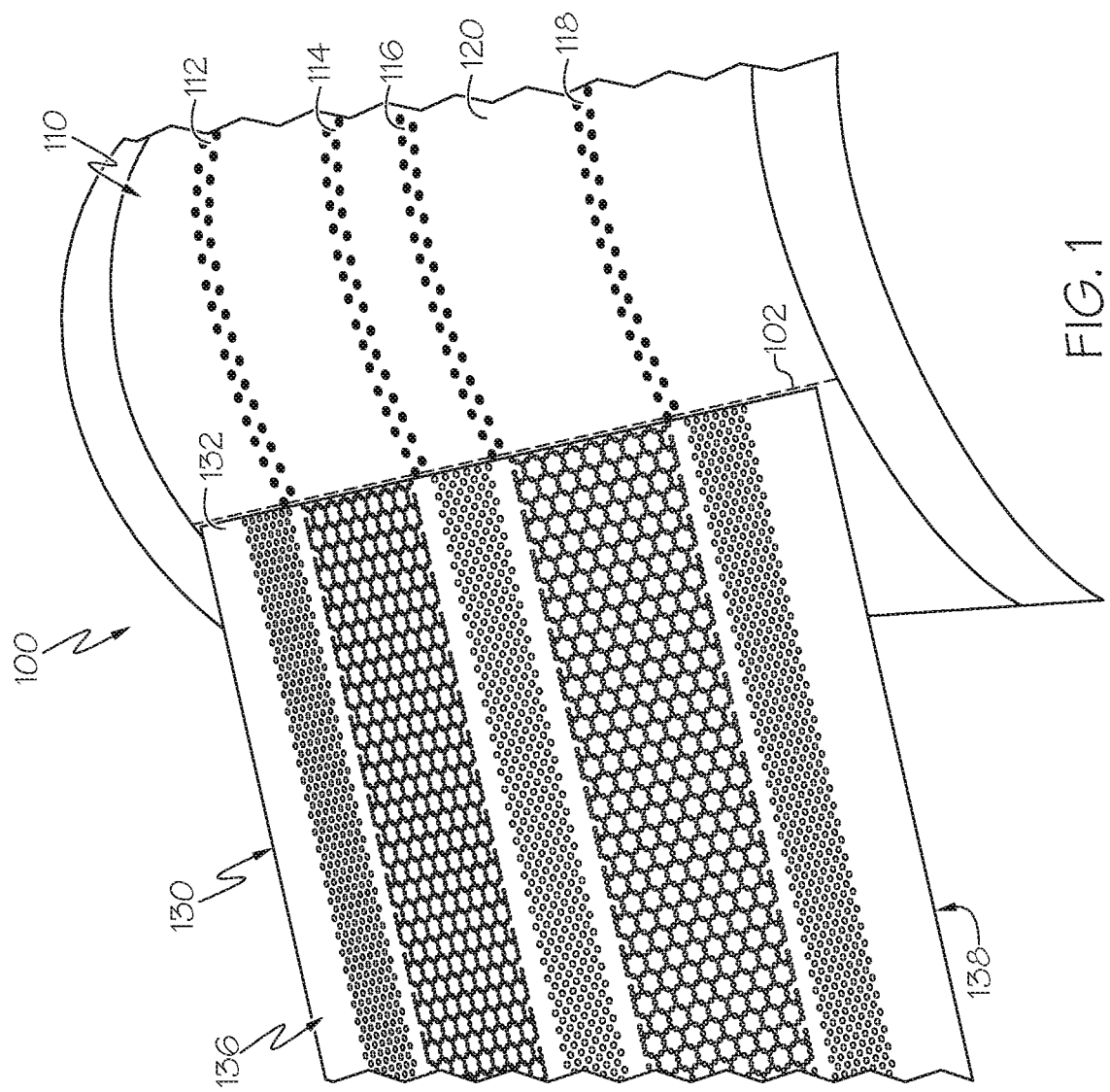
FIG. 1 illustrate an exemplary apparatus for ultrasonic bonding of elastic laminates including a rotating roll with a removable shell layer according to one or more embodiments shown and described herein.

Embodiments of the present disclosure generally relate to systems, apparatuses, and methods of ultrasonically bonding elastic laminates, and more particularly, systems, apparatuses and methods for assembling elastic laminates that may be used to make absorbent article components. A system can include an anvil that includes a rotating roll having an axis of rotation and an exterior surface. A removable shell layer can be configured to removably attach to at least a portion of the exterior surface of the rotating roll. The removable shell layer can include one or more patterned segments. The one or more patterned segments may include a plurality of shell channels formed through the removable shell layer to form a pattern. Further, the system can include an anchoring mechanism configured to anchor and fasten each patterned segment to anchoring mechanisms of the rotating roll. The removable shell layer 130 can be removed or replaced with a new removable shell layer 130 such that different patterns can be formed on absorbent articles without requiring complete replacement of an entire assembly. This may reduce cost, increase efficiency, and allow for greater variations in patterns on absorbent articles.

The following term explanations may be useful in understanding the present disclosure:

"Absorbent article" is used herein to refer to consumer products whose primary function is to absorb and retain soils and wastes. Absorbent articles can include sanitary napkins, tampons, panty liners, interlabial devices, wound dressings, wipes, disposable diapers including taped diapers and diaper pants, inserts for diapers with a reusable outer cover, adult incontinent diapers, adult incontinent pads, and adult incontinent pants. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner). "Diaper" is used herein to refer to an absorbent article generally worn by infants and incontinent persons about the lower torso.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed or pre-fastened by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed). Example diaper pants in various configurations are disclosed in U.S. Pat. Nos. 4,940,464; 5,092,861; 5,246,433; 5,569,234; 5,897,545; 5,957,908; 6,120,487; 6,120,489; 7,569,039; 8,945,326; 9,039,855; 9,050,213; and 9,028,632, all of which are incorporated by reference herein.

An "elastic," "elastomer" or "elastomeric" refers to materials exhibiting elastic properties, which include any material that upon application of a force to its relaxed, initial length can stretch or elongate to an elongated length more than 50% greater than its initial length and will substantially recover back to a length that is about 10% greater than the initial length or less upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

The term "substrate" is used herein to describe a material which is primarily two-dimensional (i.e. in an XY plane) and whose thickness (in a Z direction) is relatively small (i.e. $\frac{1}{10}$ or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may include two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

"Consolidation," "consolidating," and "consolidated" refers to a material undergoing a reduction in elongation from a first stretched length to a second stretched length that is less than the first stretched length and greater than zero.

"Relaxed state" defines a length of material when not stretched by an applied force.

In the context of the present description, an elongation of 0% refers to a material in relaxed state having a relaxed length of L, and elongation of 150% represents 2.5× the relaxed length, L, of the material. For example, an elastic film having a relaxed length of 100 millimeters would have a length of 250 millimeters at 150% elongation. And an elastic film having a relaxed length of 100 millimeters would have a length of 180 millimeters at 80% elongation.

Figure 2:
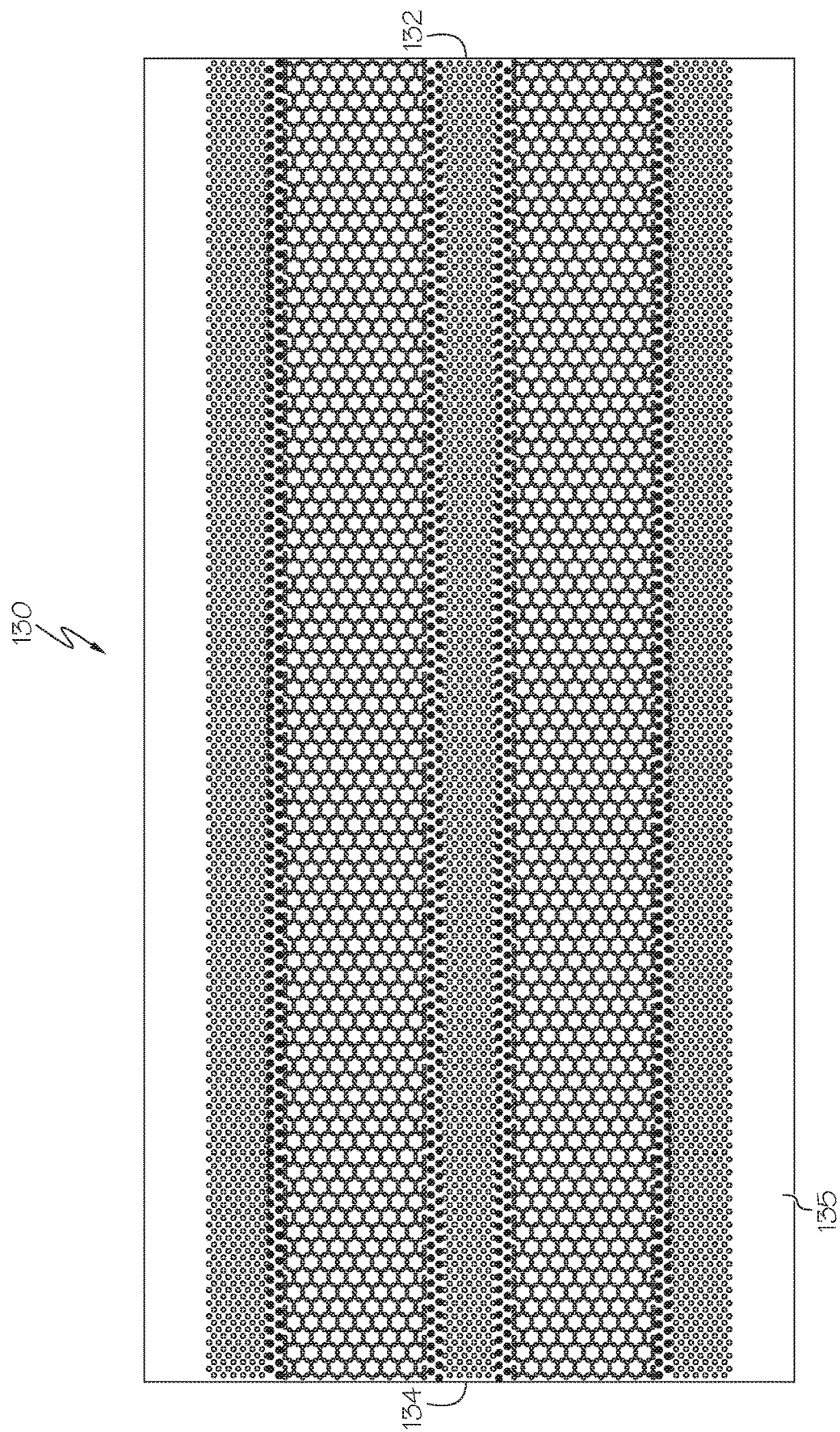
FIG. 2 illustrates the removable shell layer of FIG. 1 in a plan view, according to one or more embodiments shown and described herein.
Figure 3:
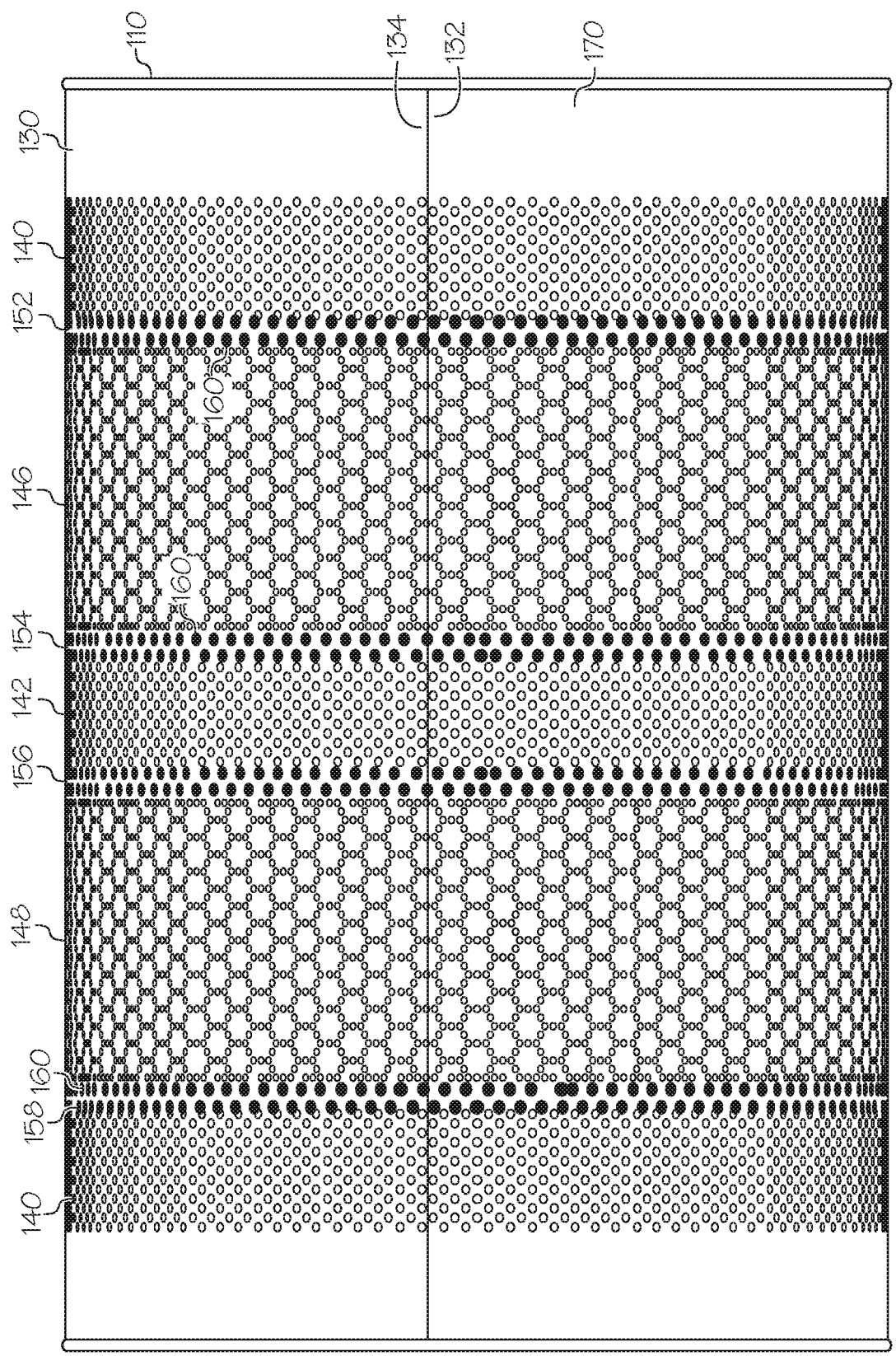
FIG. 3 illustrates the removable shell layer of FIG. 1 attached to the external surface of a rotating roll according to one or more embodiments shown and described herein.

Referring to the figures in detail, FIGS. 1-3 illustrate an exemplary apparatus 100 for ultrasonic bonding of elastic laminates including a rotating roll 110 with a removable shell layer 130. In FIG. 1, the removable shell layer 130 is in the process of being attached to a rotating roll 110. The rotating roll 110 includes an exterior surface 120 formed radially about an axis of rotation. FIG. 2 illustrates the removable shell layer 130 in a plan view, and FIG. 3 illustrates the removable shell layer 130 attached to the exterior surface 120 of the rotating roll 110.

The rotating roll 110 may combine substrates and elastic materials to form an elastic laminate as described herein. It is to be appreciated that the substrates and elastic materials may be configured in various ways. For example, the substrates may be configured as nonwovens, and the elastic materials may be configured as elastic films and/or elastic laminates.

The removable shell layer 130 can include a body 135 having a first edge 132 and a second edge 134 (FIGS. 2 and 3). The body 135 may include a garment facing or external side 136 and a rotating roll facing or internal side 138. The body 135 may be radially wrapped around the exterior surface 120 or other portion of the rotating roll 110 such that the first edge 132 abuts the second edge 134.

In embodiments, the body 135 may include a preselected size and shape. In examples, the length and width of the body 131 may be selected based on the size of the exterior surface 120 of the rotating roll 110. Moreover, the thickness of the body 135 may be selected based on the material utilized for the body 135. For instance, the body 135 may be a predetermined thickness to allow the body 135 to be bent or deformed around the exterior surface 120, while providing structural strength to general prevent or reduce cracking or other damage to the body 135. The material utilized may be a metal or alloy, such as steel, aluminum, or other material. While FIG. 2 illustrates the removable shell layer 130 as having a unitarily constructed body 135, it is noted that the body 135 may be formed of a plurality of sections or disparately formed segments that can be attached together and/or to the rotating roll 110. The plurality of removable segment can be configured to removably attach to at least the portion of the exterior surface 120 of the rotating roll 110 to partially or substantially cover the exterior surface 120 of the rotating roll 110.

Still referring to FIGS. 1-3, the removable shell layer 130 can include one or more patterned segments, such as pattern segments 140, 142, 144, 146, and 148 of FIG. 3. The pattern segments 140, 142, 144, 146, and 148 may include protrusions arranged in a predetermined pattern and/or shape. The protrusions extend radially outward from the external side 136 of the body 135. During an ultrasonic bonding process, energy is applied to impart bonds into an elastic laminate to correspond with patterns and/or shapes defined by the pattern segments 140, 142, 144, 146, and 148. It is noted that the pattern segments 140, 142, 144, 146, and 148 may be arranged to form any appropriate shape, such as n-sided polygonal shapes (where n is a number), lines, zig-zags, alphanumerical shapes, hearts, stars, or other desired shapes. In some examples, the pattern segments 140, 142, 144, 146 and 148 may include a plurality of shell channels formed through the removable shell layer to form a pattern. Moreover, each pattern segment 140, 142, 144, 146, and 148 may include the same, similar, or different patterns or shapes.

As shown in FIG. 3, the pattern segments 140, 142, 144, 146, and 148 may be configured such that the pattern is generally unbroken and/or uninterrupted where the first edge 132 and the second edge 134 interface. Accordingly, the rotating roll 110 may be utilized to continuously impart patterns as it is rotated. Additionally, the pattern segments 140, 142, 144, 146, and 148 may be utilized in aligning or assisting in aligning the first edge 132 with the second edge 134.

Moreover, as further shown in FIGS. 1 and 3, the exterior surface 120 of the rotating roll 110 may include a plurality of vacuum apertures or plurality of roll channels 112, 114, 116, and 118 (FIG. 1) formed through the exterior surface 120. The plurality of roll channels 112, 114, 116, and 118 may be fluidly connected to a vacuum source (e.g., vacuum source 402 of FIG. 4) through an air tunnel network of the rotating roll 110. The removable shell layer 130 further includes a plurality of shell channels 152, 154, 156, and 158 formed through the removable shell layer 130. When the removable shell layer 130 is attached to the exterior surface 120, the plurality of shell channels 152, 154, 156, and 158 and the plurality of roll channels 112, 114, 116, and 118 are fluidly connected. The rotating roll 110 includes an air tunnel network that is configured to fluidly connect to the plurality of roll channels 112, 114, 116, and 118, and the plurality of shell channels 152, 154, 156, and 158. During an ultrasonic bonding process, the air tunnel network may apply vacuum pressure through the plurality of roll channels 112, 114, 116, and 118 and the plurality of shell channels 152, 154, 156, and 158 that are fluidly connected and aligned to enable a vacuum action in a vacuum path on a substrate. It is noted that the vacuum source (e.g., vacuum source 402 of FIG. 4) may be disposed within the rotating roll 110 and configured to automate the vacuum pressure through the plurality of roll channels 112, 114, 116, and 118 and the plurality of shell channels 152, 154, 156, and 158. As described herein, the vacuum pressure may hold or assist in holding substrates to the rotating roll 110. The removable shell layer 130 and/or exterior surface 120 may include a plurality of support members extending across one or more of the plurality of roll channels 112, 114, 116, and 118 and the plurality of shell channels 152, 154, 156, and 15 to the help prevent the elastic material from being drawn into the channels 124 by the vacuum air pressure.

In at least some embodiments, the removable shell layer 130 may include a plurality of nubs 160 (FIG. 3) that protrude radially outward from the external side 136 of the removable shell layer 130. The plurality of nubs 160 may be arranged in a pattern (e.g., a nub pattern), which may allow for formation of patterns on an elastic laminate. The plurality of nubs 160 may further act to help prevent the elastic laminate from sliding into the plurality of roll channels 112, 114, 116, and 118 and/or the plurality of shell channels 152, 154, 156, and 158. It is to be appreciated that additional nubs 160 may be positioned inboard or outboard of the plurality of roll channels 112, 114, 116, and 118 and/or the plurality of shell channels 152, 154, 156, and 158. Moreover, the plurality of nubs 160 may include a first set of nubs extending a first distance from the exterior surface and a second set of nubs extending a second distance from the exterior surface. For instance, second set of nubs may be located near the plurality of roll channels 112, 114, 116, and 118 and/or the plurality of shell channels 152, 154, 156, and 158, while the first set of nubs are not located bear the channels. The second set of nubs may extend radially further or shorter from the external side 136 of the removable shell layer 130. In some embodiments, having the nubs proximal channels being shorter may allow for increased vacuum action. However, in other embodiments, having the nubs proximal channels being longer may be desired.

In embodiments, the exterior surface 120, removable shell layer 130, or other portion of the rotating roll 110 includes an anchoring mechanism 170 configured to anchor or fasten the removable shell layer 130 to the exterior surface 120. For instance, the anchoring mechanism 170 may include cooperating mechanism on the exterior surface 120 and the removable shell layer 130, such as opposing magnets which may attract the exterior surface 120 to the removable shell layer 130.

Still referring to FIGS. 1-3, the anchoring mechanism 170 can include a plurality of magnets, mechanical anchoring mechanisms, or combinations thereof disposed at least one of within or on the exterior surface 120, wherein the plurality of magnets, mechanical anchoring mechanisms, or combinations thereof are configured to attach to the removable shell layer 130 to fasten the removable shell layer 130 to the rotating roll 110.

In embodiments, such mechanical anchoring mechanisms can include a leading edge interlock disposed at the first edge 132 of the removable shell layer 130 and a trailing edge interlock disposed at a trailing edge of the removable shell layer 130 wherein the leading edge interlock is configured to interface with the trailing edge interlock. According to an embodiment, the leading edge interlock may be a male or female edge that engages with the trailing edge, where the trailing edge includes a complimentary male or female edge, such as ridges, slots, channels, protrusions, or the like. In another embodiment, the mechanical interlock can include one or more protrusions removably engagable with one or more pockets to anchor the removable shell layer 130 to the exterior surface 120, and wherein at least one of the exterior surface 120 or the removable shell layer 130 includes the one or more protrusions, and the other of the exterior surface 120 or the removable shell layer 130 includes the one or more pockets.

In an example, the anchoring mechanism 170 can include a plurality of magnets disposed at least one of within or on the exterior surface 120, wherein the plurality of magnets are configured to magnetically attach to one or more magnets of the removable shell layer 130 to fasten the removable shell layer 130 to the rotating roll 110. In at least some examples, the plurality of magnets may be disposed at various locations about the rotating roll 110 and the removable shell layer 130, such as along the first edge 132 and the second edge 134, at or proximal the one or more pattern segments 140, 142, 144, 146, and 148, at or proximal the plurality of roll channels 112, 114, 116, and 118, and/or at or proximal the plurality of shell channels 152, 154, 156, and 158.

In an embodiment, the plurality of magnets can form a first magnetized zone of the rotating roll 110 and a second magnetized zone of the rotating roll 110. The first magnetized zone can be configured to anchor a leading edge or first edge 132 of the removable shell layer 130 and a trailing edge or second edge 134 of the removable shell layer 130. The first magnetized zone can include a higher magnetism than the second magnetized zone. As such, the strengths of magnets may vary as appropriate. For instance, the strength of magnets may increase along the first edge 132 and the second edge 134 in comparison with other portions of the body 135. Moreover, the strength of magnets may increase at or proximal the plurality of roll channels 112, 114, 116, and 118, and/or at or proximal the plurality of shell channels 152, 154, 156, and 158.

Moreover, the anchoring mechanism 170 can include other mechanisms, such as a threaded member that secures the removable shell layer 130 to the exterior surface 120. In another example, the anchoring mechanism 170 can include a recessed pocket and an angled end, and wherein at least one of the exterior surface 120 or the removable shell layer 130 includes the recessed pocket, and the other of the at least one of the exterior surface 120 or the removable shell layer 130 includes at least one angled end configured to be inserted within the recessed pocket to apply circumferential tension. The angled end can be inserted within the recessed pocket and may secure the removable shell layer 130 via a friction fit. It is noted that various anchoring mechanism 170 may be used in combination, such as an angled end and recessed pocket utilized in combination with a plurality of magnets.

In another embodiment, the anchoring mechanism 170 can include one or more protrusions or pins removably engagable with one or more pockets or apertures to anchor the removable shell layer 130 to the exterior surface 120. The exterior surface 120 or the removable shell layer 130 includes the one or more protrusions, and the other of the exterior surface 120 or the removable shell layer 130 includes the one or more pockets. As such, the exterior surface 120 or the removable shell layer 130 can include complementary formations that enable the anchoring mechanism 170 to anchor the exterior surface 120 to the removable shell layer 130.

For instance, the anchoring mechanism 170 can include a plurality of pins extending radially from the exterior surface 120 along a split line 102 (FIG. 1). The anchoring mechanism 170 further includes a plurality of apertures formed in or through the removable shell layer 130 and configured to receive the plurality of pins. The pins may be generally D-shaped or may include other shapes. The pins may be rotated from a loading to a locking position within the apertures. The plurality of pins extend radially a smaller height than a plurality of nubs 160 extending from the removable shell layer 130. The pins may interlock with the apertures to secure the removable shell layer 130 to the exterior surface 120.

Figure 4:
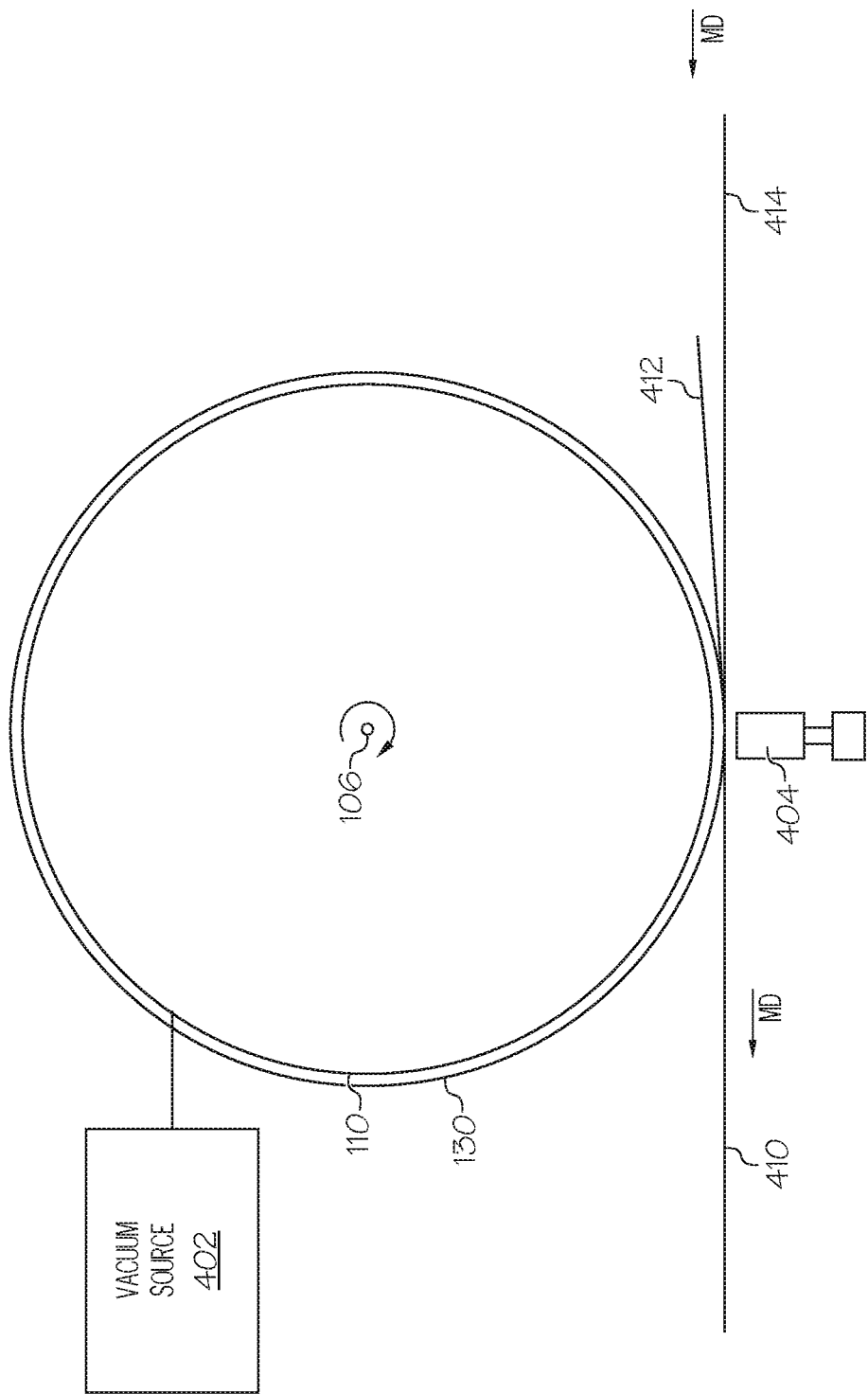
FIG. 4 illustrates a schematic side view of an apparatus configured to assemble elastic laminates according to one or more embodiments shown and described herein.

Referring now to FIG. 4, there is a schematic side views of an apparatus 100 configured to assemble elastic laminates. As shown in FIGS. 1-3, the apparatus includes a rotating roll 110 having a removable shell layer 130 and an exterior surface 120. The rotating roll 110 may be referred to as an anvil in an ultrasonic bonding process.

The rotating roll 110 is adapted to rotate in a first direction Dir1 about an axis of rotation 106. Although the first direction Dir1 is depicted as clockwise, it is to be appreciated that the rotating roll 110 may be configured to rotate such that the first direction Dir1 is counterclockwise.

As shown in FIGS. 1, 3, and 4, the rotating roll 110, and more particularly, the exterior surface 120 may also be fluidly connected with a vacuum source 402. As such, vacuum source 402 may generate vacuum air pressure to hold or assist in holding one or more substrates, such as substrate 414 and one or more laminate materials 412 onto the exterior surface 120 of the rotating roll 110 during operation. The exterior surface 120 of the rotating roll 110 may include one or more plurality of roll channels 112, 114, 116, and 118 (FIG. 1) which may include apertures fluidly connected with the vacuum source 402. In turn, the roll channels 112, 114, 116, and 118 may define a vacuum zone extending axially or in the cross direction CD.

The laminate material 412 and substrates 414 can include elastic materials, such as elastic films, which may include one or more layers (e.g., a base layer, a surface layers or skin, etc.). During formation, the films may be extended or stretched to create a plurality of cracks and tears in the skins at a microscopic scale, wherein such cracks and tears may help reduce the skin contribution to the extension forces of the elastic film. The apparatus 100 may also include a spreader mechanism which may operate to activate the elastic material by stretching the elastic material in a MD to a first elongation during the elastic laminate assembly process. The stretched elastic material is then consolidated to a second elongation, wherein the second elongation is less than the first elongation. The elastic material is advanced from the spreader mechanism onto a substrate on the rotating roll 110. It is to be appreciated that the apparatus 100 may include more than one spreader mechanisms configured in various ways, such as disclosed for example in U.S. Patent Pub. No. 2021/0085532A1.

In embodiments, stretched elastic materials and substrates are combined on the rotating roll 110. The combined substrates and elastic materials may then be ultrasonically bonded together on the rotating roll 110 to form elastic laminates. The apparatus 100 may include one or more ultrasonic mechanisms 404 adjacent the rotating roll 110. The ultrasonic mechanism 404 includes a horn configured to impart ultrasonic energy to the combined substrates and elastic materials on the rotating roll 110. In at least some examples, the ultrasonic mechanism 404 or a separate heater may apply heat to the laminate material assembly at least one of before, during, or after the ultrasonically bonding.

As described herein, the removable shell layer 130 includes pattern segments 140, 142, 144, 146, and 148 extending radially outward from the external side 136 of the body 135. The ultrasonic mechanisms 404 may apply energy to create resonance at frequencies and amplitudes so a horn of the ultrasonic mechanisms 404 vibrates rapidly in a direction generally perpendicular to the substrates and elastic materials being advanced past the ultrasonic mechanisms 404 on the removable shell layer 130. The vibration generates heat to melt and bond the substrates and elastic material together in areas supported by the pattern segments 140, 142, 144, 146, and 148 on the removable shell layer 130. During the ultrasonic bonding process, bonds imparted into the elastic laminate from the ultrasonic mechanism 404 may correspond with patterns and/or shapes defined by the pattern segments 140, 142, 144, 146, and 148. It is to be appreciated that an elastic laminate 410 may include various portions of components bonded together in various ways and with differing or identical bond patterns. It is to be appreciated that the apparatus 100 may be adapted to create various types of bond configurations, such as disclosed, for example, in U.S. Pat. No. 6,572,595.

Further, the ultrasonic mechanisms 404 may be configured in various ways, such as disclosed for example in U.S. Pat. Nos. 3,113,225; 3,562,041; 3,733,238; 6,036,796; 6,508,641; and 6,645,330. In some configurations, the ultrasonic mechanism may be configured as a linear oscillating type sonotrode. In some configurations, the sonotrode may include a plurality of sonotrodes nested together in the cross direction CD.

In various embodiments, the apparatus 100 described herein may operate to assemble elastic laminates configured in various ways. For instance, substrates 414 and/or laminate material 412 may be advanced in MD or otherwise onto the rotating roll 110. During the assembly process, a spreader mechanism activates an elastic material by stretching the elastic material to a first elongation in the cross direction CD. The stretched elastic material is then consolidated to a second elongation that is less than the first elongation. And the consolidated elastic material is positioned into contact with the second surface of the first substrate 414. The stretched elastic material may be consolidated before advancing to the rotating roll 110, and in some configurations, the elastic material may be consolidated after advancing to the rotating roll 110. In turn, the elastic laminate 410 may be formed by ultrasonically bonding the first substrate 414 and the elastic laminate material 412 together with a second substrate on the rotating roll 110

Figure 5:
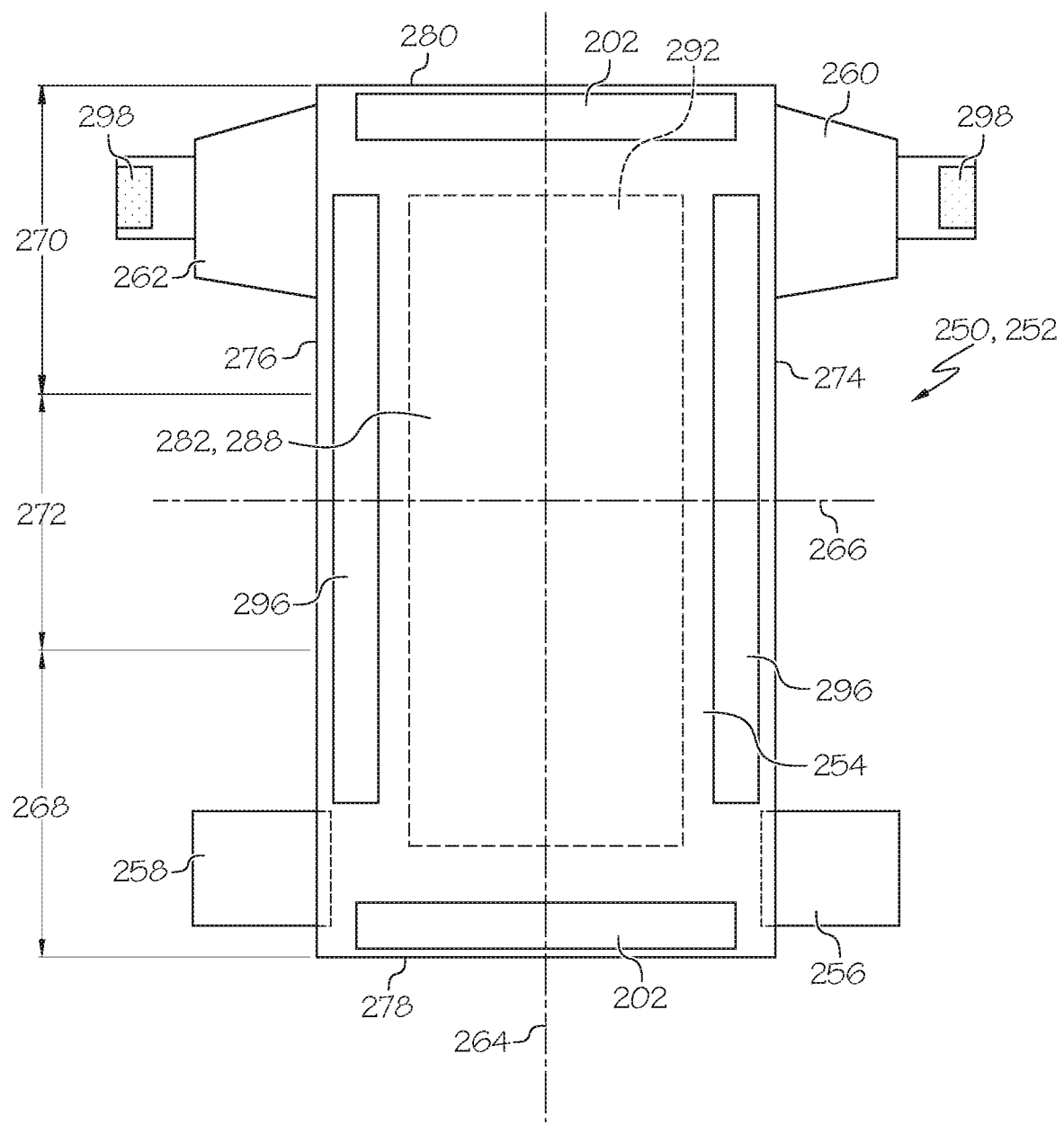
FIG. 5 illustrates a plan view of an absorbent article that includes one or more elastic laminates assembled during manufacture according to one or more embodiments shown and described herein.

Referring now to FIG. 5, there is a plan view of an absorbent article that includes one or more elastic laminates assembled during manufacture. As described herein, apparatuses and methods of the present disclosure may be utilized to assembly various forms of elastic laminates used in the manufacture of absorbent articles. Such elastic laminates may be utilized in absorbent article components such as, for example: backsheets, topsheets, absorbent cores, front and/or back ears, fastener components, and various types of elastic webs and components such as leg elastics, barrier leg cuff elastics, and waist elastics. The absorbent article 250 may include one or more elastic laminates assembled during manufacture according to the apparatuses and methods disclosed herein with the portion of the absorbent article 250 with the portion of the diaper that faces toward a wearer visible in the plan view of FIG. 5.

For the purposes of a specific illustration, FIG. 5 shows an example of a disposable absorbent article 250 in the form of a diaper 252 that may be constructed from such elastic laminates manipulated during manufacture according to the apparatuses and methods disclosed herein. The diaper 252 includes a chassis 254 having a first ear 256, a second ear 258, a third ear 260, and a fourth ear 262. The chassis 254 can include with a longitudinal axis 264 and a lateral axis 266. The chassis 254 can include a first waist region 268, a second waist region 270, and a crotch region 272 disposed intermediate the first and second waist regions. The periphery of the chassis 254 may be defined by a pair of longitudinally extending side edges 274, 276; a first outer edge 278 extending laterally adjacent the first waist region 268; and a second outer edge 280 extending laterally adjacent the second waist region 270.

In embodiments, the chassis 254 includes an inner, body-facing surface 282, and an outer, garment-facing surface (not shown). The chassis 254 of the diaper 252 may include a topsheet 288 defining the inner, body-facing surface 282, and a backsheet (not shown) defining the outer, garment-facing surface. An absorbent core 292 may be disposed between a portion of the topsheet 288 and the backsheet. As discussed in more detail below, any one or more of the regions may be stretchable and may include an elastomeric material or laminate as described herein. As such, the diaper 252 may be configured to adapt to a specific wearer's anatomy upon application and to maintain coordination with the wearer's anatomy during wear.

The diaper 252 may include an elastic waist feature 202. The elastic waist feature 202 may include a waist band and may provide improved fit and waste containment. The elastic waist feature 202 may be configured to elastically expand and contract to dynamically fit the wearer's waist. The elastic waist feature 202 can be incorporated into the diaper and may extend at least longitudinally outwardly from the absorbent core 292 and generally form at least a portion of the first and/or second outer edges 278, 280 of the diaper 252. In addition, the elastic waist feature may extend laterally to include the ears. While the elastic waist feature 202 or any constituent elements thereof may include one or more separate elements affixed to the diaper 252, the elastic waist feature may be constructed as an extension of other elements of the diaper, such as the backsheet, the topsheet 288, or both the backsheet and the topsheet 288. In addition, the elastic waist feature 202 may be disposed on the outer, garment-facing surface of the chassis 254; the inner, body-facing surface 282; or between the inner and outer facing surfaces. The elastic waist feature 202 may be constructed in a number of different configurations including those described in U.S. Pat. Nos. 8,697,938 and 8,777,917, all of which are hereby incorporated by reference herein.

Still referring to FIG. 5, the diaper 252 may include leg cuffs 296 that may provide improved containment of liquids and other body exudates. In particular, elastic gasketing leg cuffs can provide a sealing effect around the wearer's thighs to prevent leakage. It is to be appreciated that when the diaper 252 is worn, the leg cuffs 296 may be placed in contact with the wearer's thighs, and the extent of that contact and contact pressure may be determined in part by the orientation of diaper on the body of the wearer. The leg cuffs 296 may be disposed in various ways on the diaper 252.

The diaper 252 may be provided in the form of a pant-type diaper or may alternatively be provided with a re-closable fastening system, which may include fastener elements in various locations to help secure the diaper in position on the wearer. For example, fastener elements 298 may be located on the ears and may be adapted to releasably connect with one or more corresponding fastening elements located in the first or second waist regions. For example, the diaper 252 may include a connection zone on the first ear 256 or a second ear 258, sometimes referred to as a landing zone. It is to be appreciated that various types of fastening elements may be used with the diaper.

Figure 6:
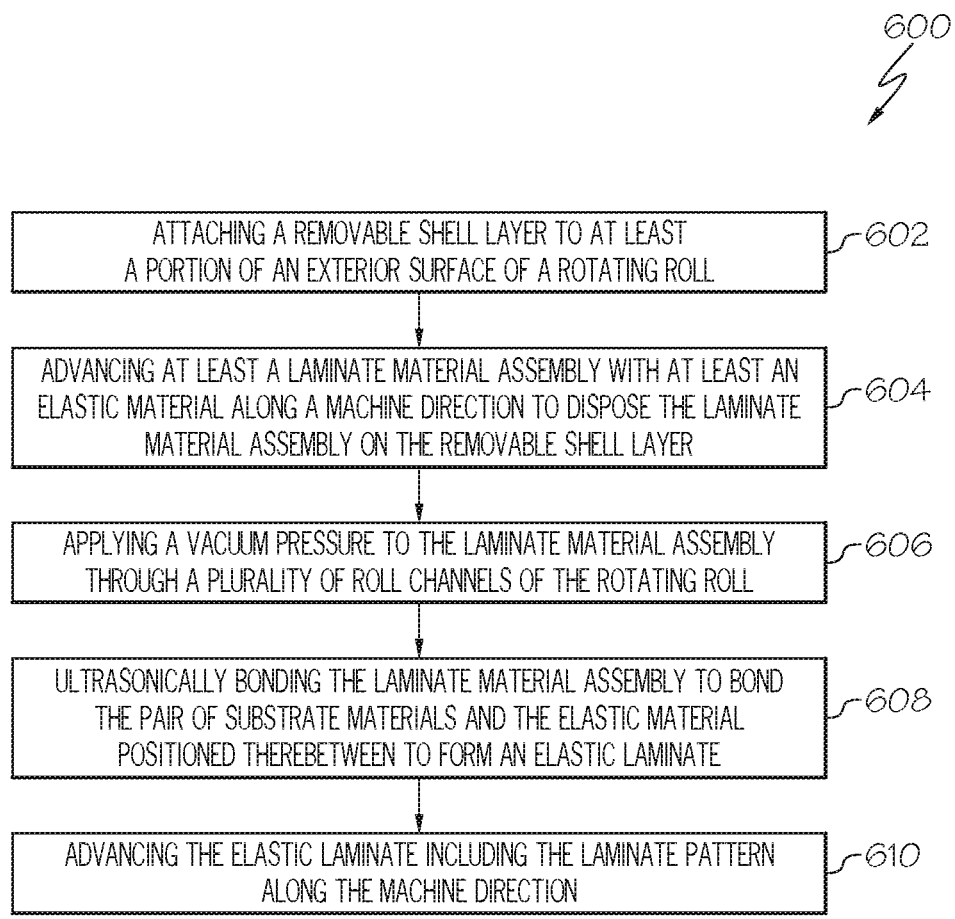
FIG. 6 illustrates a process for use with the apparatus of FIG. 4 for ultrasonically bonding elastic laminates to form an absorbent article according to one or more embodiments shown and described herein.

Turning now to FIG. 6, a process 600 is shown for use with the apparatus 100 of FIGS. 1-4 for ultrasonically bonding elastic laminates to form an absorbent article, such as absorbent article 250 of FIG. 5. It is noted that a greater or fewer number of steps may be included without departing from the scope of the present disclosure.

At block 602 of the process 600 includes attaching a removable shell layer 130 to at least a portion of an exterior surface of a rotating roll 110. The removable shell layer 130 can include a plurality of shell channels to form a shell pattern, and the rotating roll 110 including an axis of rotation and the exterior surface 120 formed radially about the axis of rotation. The removable shell layer 130 can be attached to the rotating roll 110 by deforming the removable shell layer radially around the exterior surface 120. In other embodiments, the removable shell layer 130 can be attached as a plurality of segments. Moreover, at block 602 the removable shell layer 130 that is being attached may be replacing a prior removable shell.

As described herein, the removable shell layer 130 can be attached to the exterior surface of a rotating roll 110 via an attachment mechanism. The attachment mechanism can include mechanical attachment mechanisms, magnets, or a combination thereof. It is noted that the removable shell layer 130 can be attached to the exterior surface 120 via a manual process or automated process. In examples, the removable shell layer 130 can be tensioned on the exterior surface of a rotating roll 110 such that a method includes tensioning the removable shell layer 130.

At block 604 of the process 600 includes advancing at least a laminate material assembly with at least an elastic material along a machine direction to dispose the laminate material assembly on the removable shell layer 130. In some examples, a spreader mechanism can activate the elastic material by stretching the elastic material in a MD to a first elongation during the elastic laminate assembly process. The stretched elastic material is then consolidated to a second elongation, wherein the second elongation is less than the first elongation. The elastic material is advanced from the spreader mechanism onto a substrate on the rotating roll 110.

At block 608 of the process 600 includes applying a vacuum pressure to the laminate material assembly through a plurality of roll channels of the rotating roll. The plurality of roll channels of the rotating rolls 110 can be aligned with the plurality of shell channels of the removable shell layer 130 to draw the laminate material assembly into the plurality of shell channels forming the shell pattern. The vacuum pressure may be applied through a air tunnel network that is configured to (i) fluidly connect to the plurality of roll channels and the plurality of shell channels when the plurality of roll channels are aligned with the plurality of shell channels and (ii) apply vacuum pressure through the plurality of roll channels and the plurality of shell channels that are fluidly connected and aligned. The vacuum pressure may thus hold or assist in holding substrate and laminate materials to the rotating roll 110.

At block 608 of the process 600 includes ultrasonically bonding the laminate material assembly to bond the pair of substrate materials and the elastic material positioned therebetween to form an elastic laminate. The elastic laminate can include a laminate pattern corresponding to the shell pattern of the removable shell layer. Ultrasonically bonding the laminate material can include applying energy to impart bonds into an elastic laminate to correspond with patterns and/or shapes defined by the pattern segments. In an example, the energy can create vibrations and/or heat that cause the substrate materials and elastic materials to bond at positions of the pattern. In examples, heat can be applied to the laminate material assembly at least one of before, during, or after the ultrasonically bonding.

At block 610 of the process 600 includes advancing the elastic laminate including the laminate pattern along the machine direction. For instance, as shown in FIG. 4, the substrates and laminate materials can be processes as a roll or sheet. Thus, patterns may be formed in elastic laminates. The elastic laminates can be formed as the rotating roll rotates and a ultrasonic mechanisms applies energy to woven, non-woven and laminates.

It should now be apparent that the various embodiments illustrated and described herein may comprise ultrasonic bonding of elastic laminates, with a rotating roll and a removable shell layer. While particular reference has been made herein to products for containing consumer goods or consumer goods products themselves, it should be apparent that the ultrasonic bonding of elastic laminates with a rotating roll and a removable shell layer, as described herein, may be suitable for use in forming products for use in the consumer goods industry, the medical industry, the garment industry, and the like.

All documents cited in the Detailed Description are, in relevant part, incorporated herein by reference; the citation of any document is not to be construed as an admission that it is prior art with respect to the present disclosure. To the extent that any meaning or definition of a term in this written document conflicts with any meaning or definition of the term in a document incorporated by reference, the meaning or definition assigned to the term in this written document shall govern.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A method for ultrasonically bonding elastic laminates, the method comprising:
   attaching a removable shell layer comprising a plurality of shell channels to form a shell pattern to at least a portion of an exterior surface of a rotating roll, the rotating roll including an axis of rotation, the exterior surface formed radially about the axis of rotation;
   advancing at least a laminate material assembly comprising a pair of substrate materials with at least an elastic material positioned therebetween along a machine direction to dispose the laminate material assembly on the removable shell layer;
   applying a vacuum pressure to the laminate material assembly through a plurality of roll channels of the rotating roll aligned with the plurality of shell channels of the removable shell layer to draw the laminate material assembly into the plurality of shell channels forming the shell pattern;
   ultrasonically bonding the laminate material assembly to bond the pair of substrate materials and the elastic material positioned therebetween to form an elastic laminate including a laminate pattern corresponding to the shell pattern; and
   advancing the elastic laminate including the laminate pattern along the machine direction.

2. The method of claim 1, comprising applying heat to the laminate material assembly at least one of before, during, or after the ultrasonically bonding.

3. The method of claim 1, comprising tensioning the removable shell layer.

4. The method of claim 1, comprising replacing the removable shell layer with a new removable shell layer.

5. The method of claim 1, wherein the rotating roll comprises a roll anchoring mechanism, wherein the roll anchoring mechanism is configured to removably attach at least a portion of the removable shell layer to the rotating roll.

6. The method of claim 5, wherein the roll anchoring mechanism comprises a plurality of magnets disposed within and/or on the exterior surface of the rotating roll.

7. The method of claim 6, wherein the plurality of magnets form a first magnetized zone of the rotating roll and a second magnetized zone of the rotating roll, the first magnetized zone of the rotating roll is configured to anchor to a leading edge of the removable shell layer and to a trailing edge of the removable shell layer, and the first magnetized zone comprises a higher magnetism than the second magnetized zone.

8. A method for ultrasonically bonding elastic laminates, the method comprising:
   attaching a removable shell layer comprising a plurality of shell channels to form a shell pattern to at least a portion of an exterior surface of a rotating roll, the rotating roll including an axis of rotation, the exterior surface of the rotating roll formed radially about the axis of rotation, wherein the rotating roll comprises a roll anchoring mechanism, wherein the roll mechanism comprises a plurality of apertures formed in or through the removable shell layer and configured to receive a plurality of pins extending radially from the exterior surface of the rotating roll;
   advancing at least a laminate material assembly comprising a pair of substrate materials with at least an elastic material positioned therebetween along a machine direction to dispose the laminate material assembly on the removable shell layer;
   applying a vacuum pressure to the laminate material assembly through a plurality of roll channels of the rotating roll aligned with the plurality of shell channels of the removable shell layer to draw the laminate material assembly into the plurality of shell channels forming the shell pattern;
   ultrasonically bonding the laminate material assembly to bond the pair of substrate materials and the elastic material positioned therebetween to form an elastic laminate including a laminate pattern corresponding to the shell pattern; and
   advancing the elastic laminate including the laminate pattern along the machine direction.

9. The method of claim 8, comprising applying heat to the laminate material assembly at least one of before, during, or after the ultrasonically bonding.

10. The method of claim 8, comprising tensioning the removable shell layer.

11. The method of claim 8, comprising replacing the removable shell layer with a new removable shell layer.

12. The method of claim 8, wherein the plurality of pins extend radially at a smaller height than a plurality of nubs extending from the removable shell layer.

13. The method of claim 8, wherein the exterior surface of the rotating roll includes a plurality of roll channels formed through the exterior surface, and the removable shell layer includes a plurality of shell channels formed through the removable shell layer, and wherein the rotating roll includes an air tunnel network that is configured to (i) fluidly connect to the plurality of roll channels and the plurality of shell channels when the plurality of roll channels are aligned with the plurality of shell channels and (ii) apply vacuum pressure through the plurality of roll channels and the plurality of shell channels that are fluidly connected and aligned.

14. The method of claim 13, comprising a vacuum source disposed within the rotating roll and configured to automate the vacuum pressure through the plurality of roll channels and the plurality of shell channels.

15. A method for ultrasonically bonding elastic laminates, the method comprising:
   attaching a removable shell layer to form a shell pattern to at least a portion of an exterior surface of a rotating roll, the rotating roll including an axis of rotation, the exterior surface of the rotating roll formed radially about the axis of rotation, wherein the removable shell layer comprises a plurality of segments that each include a plurality of nubs;
   advancing at least a laminate material assembly comprising a pair of substrate materials with at least an elastic material positioned therebetween along a machine direction to dispose the laminate material assembly on the removable shell layer;
   applying a vacuum pressure to the laminate material assembly through a plurality of roll channels of the rotating roll aligned with the plurality of shell channels of the removable shell layer to draw the laminate material assembly into the plurality of shell channels forming the shell pattern;
   ultrasonically bonding the laminate material assembly to bond the pair of substrate materials and the elastic material positioned therebetween to form an elastic laminate including a laminate pattern corresponding to the shell pattern; and advancing the elastic laminate including the laminate pattern along the machine direction.

16. The method of claim 15, comprising applying heat to the laminate material assembly at least one of before, during, or after the ultrasonically bonding.

17. The method of claim 15, wherein the plurality of nubs comprises a first set of nubs extending a first distance from an exterior surface of the removable shell layer and a second set of nubs extending a second distance from the exterior surface of the removable shell layer, and wherein the first distance is different than the second distance.

18. The method of claim 15, wherein the rotating roll comprises a roll anchoring mechanism, wherein the roll anchoring mechanism is configured to removably attach at least a portion of the removable shell layer to the rotating roll.

19. The method of claim 18, wherein the roll anchoring mechanism comprises a plurality of magnets disposed within and/or on the exterior surface of the rotating roll.

20. The method of claim 19, wherein the plurality of magnets form a first magnetized zone of the rotating roll and a second magnetized zone of the rotating roll, the first magnetized zone of the rotating roll is configured to anchor to a leading edge of the removable shell layer and to a trailing edge of the removable shell layer, and the first magnetized zone comprises a higher magnetism than the second magnetized zone.

* * * * *